United States Patent
Hareland et al.

(10) Patent No.: US 9,539,431 B2
(45) Date of Patent: Jan. 10, 2017

(54) EVENT TRIGGERED PROGNOSTICS

(71) Applicant: Medtronic, Inc., Minneapolis, MN (US)

(72) Inventors: Scott A. Hareland, Lino Lakes, MN (US); Leonard P. Radtke, East Bethel, MN (US)

(73) Assignee: Medtronic, Inc., Minneapolis, MN (US)

( * ) Notice: Subject to any disclaimer, the term of this patent is extended or adjusted under 35 U.S.C. 154(b) by 254 days.

(21) Appl. No.: 14/058,699

(22) Filed: Oct. 21, 2013

(65) Prior Publication Data

US 2014/0379039 A1    Dec. 25, 2014

Related U.S. Application Data

(60) Provisional application No. 61/837,678, filed on Jun. 21, 2013.

(51) Int. Cl.
  *A61N 1/37*    (2006.01)
  *A61N 1/372*   (2006.01)
  *A61B 5/0452*  (2006.01)

(52) U.S. Cl.
  CPC ......... *A61N 1/37252* (2013.01); *A61B 5/0452* (2013.01); *A61N 1/3706* (2013.01); *A61B 2560/0276* (2013.01); *A61N 1/37235* (2013.01); *A61N 1/37258* (2013.01)

(58) Field of Classification Search
  CPC .............. A61N 1/37252; A61N 1/3706; A61N 1/37235; A61N 1/37258; A61B 5/0452; A61B 2560/0276
  See application file for complete search history.

(56) References Cited

U.S. PATENT DOCUMENTS

| | | | |
|---|---|---|---|
| 6,021,352 A | 2/2000 | Christopherson et al. | |
| 7,031,771 B2 | 4/2006 | Brown et al. | |
| 7,089,057 B2 | 8/2006 | Heathershaw et al. | |
| 7,389,144 B1 | 6/2008 | Osorio et al. | |
| 7,454,249 B1* | 11/2008 | Bornzin et al. | 607/27 |
| 7,844,337 B2 | 11/2010 | Hoyme et al. | |
| 8,155,758 B2 | 4/2012 | Roline et al. | |
| 8,170,670 B2 | 5/2012 | Stubbs et al. | |
| 8,290,753 B2 | 10/2012 | Tryon, III et al. | |
| 8,406,892 B2 | 3/2013 | Kallis | |
| 8,442,635 B2 | 5/2013 | Bohn et al. | |
| 2004/0064161 A1* | 4/2004 | Gunderson | A61B 5/0424 607/28 |
| 2006/0009951 A1 | 1/2006 | Tryon, III et al. | |
| 2006/0230313 A1 | 10/2006 | Grichnick et al. | |
| 2008/0103542 A1 | 5/2008 | Hoyme et al. | |
| 2010/0023082 A1 | 1/2010 | Dong et al. | |
| 2010/0114222 A1 | 5/2010 | Gunderson et al. | |
| 2010/0179820 A1 | 7/2010 | Harrison et al. | |

* cited by examiner

*Primary Examiner* — Rex R Holmes
(74) *Attorney, Agent, or Firm* — Evans M. Mburu

(57) ABSTRACT

The present disclosure describes an implantable medical device utilizing an event-triggered prognostic indicator. The disclosure describes techniques for prognostics and management of implantable medical systems to facilitate continuity of performance of sensing and therapy delivery functions by providing adequate response time to handle emerging issues prior to adverse clinical impacts. In accordance with the present disclosure, event-triggered prognostic indicators facilitate the identification of potential device conditions.

12 Claims, 6 Drawing Sheets

EVENT TRIGGERED PROGNOSTICS

CROSS-REFERENCE TO RELATED APPLICATION

This application claims priority to provisional U.S. Application No. 61/837,678, filed Jun. 21, 2013, which is incorporated herein by reference in its entirety.

FIELD

The present disclosure relates to implantable medical devices. More particularly, this disclosure pertains to detection of device conditions of the implantable medical devices.

BACKGROUND

A wide variety of implanted medical devices (IMDs) for delivering a therapy or monitoring a physiologic condition which can employ one or more elongated electrical leads and/or sensors are available. Such IMDs can monitor or deliver therapy to the heart, muscle, nerve, brain, and stomach or other organs.

Examples of such IMDs include implantable cardioverter/defibrillators (ICD), implantable pulse generators (IPG) and pacemaker/cardioverter/defibrillators (PCD) that provide sensing of arrhythmias and programmable staged therapies including pacing regimens and cardioversion energy and defibrillation energy shock regimens in order to terminate a sensed arrhythmia with the most energy efficient and minimally traumatic therapies.

In such IMDs, the integrity of the device is of great importance. The IMDs are desired to be capable of reliable operation and be designed for safety. The implanted IMD are desired to be capable of autonomous operation without active or continuous external monitoring. This is because patients with the IMDs typically resume normal activities of daily life shortly after the implant is performed.

Moreover, the IMDs are desired to consume low power due to the balance needed between device longevity to reduce surgical replacement burden and the miniaturization of the IMDs for comfort and cosmetic reasons. Strict power management constraints are placed on electronics design, and extensive and creative power management and ultra-low power electronic design techniques are desired for the IMDs. This focus precludes the use of many commercially available prognostic sensors, and limits the ability to run computationally expensive firmware algorithms for routine prognostic analysis. As a point of reference, various commercially available prognostic sensors consume more power than the entire power budget of an implantable medical device, where the average power consumption in a modern pacemaker is on the order of tens of microwatts.

Many of the conventional solutions employed in IMDs for fault detection have utilized periodic testing that includes measurements of one or more parameters to determine whether the integrity of the IMD is compromised. One of the challenges associated with the conventional solutions is that the periodic measurements may not always detect with the intermittent nature of the various device conditions that may impact the IMD operation. Additionally, the periodic measurements may not identify device conditions expeditiously for effective containment and to prevent error propagation.

Techniques are needed that will support continuous real-time monitoring and identification of device conditions to prevent error propagation that may lead to adverse performance of an IMD.

SUMMARY

One of the difficulties stemming from the conventional techniques for evaluating the reliability of an implantable medical device (IMD) is the need for integrating additional sensors to monitor the performance of the IMD. The inventors of the present application have observed that the desire for ultra-low power IMD designs constrains the ability to perform continuous real-time monitoring that would facilitate the identification of device conditions that impact the IMD operation. In that context, prognostics can play a large role in managing not only the patient, but the IMD as well.

In accordance with the foregoing, a system is provided having a medical electrical lead coupled to an IMD. The IMD includes a housing having electronics for performing therapy delivery and sensing functions.

In general, exemplary embodiments of the present disclosure provide leading indicators and system-critical indicators of device conditions based on real time monitoring associated with the physiological signals and the therapy delivery. In some embodiments, a device monitoring system that may operate in a continuous, real-time manner is utilized. The embodiments disclose monitoring a signal pertaining to an event to obtain leading indicators and system-critical indicators and activating a diagnostic evaluation of a component associated with the event based on the indicators.

In one embodiment, a sensor derives a first plurality of parameters associated with a function of the IMD. A control module evaluates the first plurality of parameters to determine whether a first threshold has been met and activates a diagnostic evaluation of a component associated with performing the function in response to the first threshold being met.

In another embodiment, a method of monitoring an IMD includes deriving a first plurality of parameters associated with a function of the IMD, evaluating the first plurality of parameters to determine whether a first threshold has been met, and activating a diagnostic evaluation of a component associated with performing the function in response to the first threshold being met.

The foregoing summary information is intended to merely illustrate some of the aspects and features of the present disclosure and is not meant to limit the scope in any way. In fact, upon review of the foregoing and the following described and depicted embodiments one of skill in the art will surely recognize insubstantial modifications or extensions of the disclosure each of which is expressly intended to be covered hereby.

BRIEF DESCRIPTION

Various aspects and features of the present disclosure will be readily appreciated as the same becomes better understood by reference to the detailed description when considered in connection with the accompanying drawings, in which like reference numerals designate like parts throughout the figures thereof and wherein.

DETAILED DESCRIPTION

Figure 1:
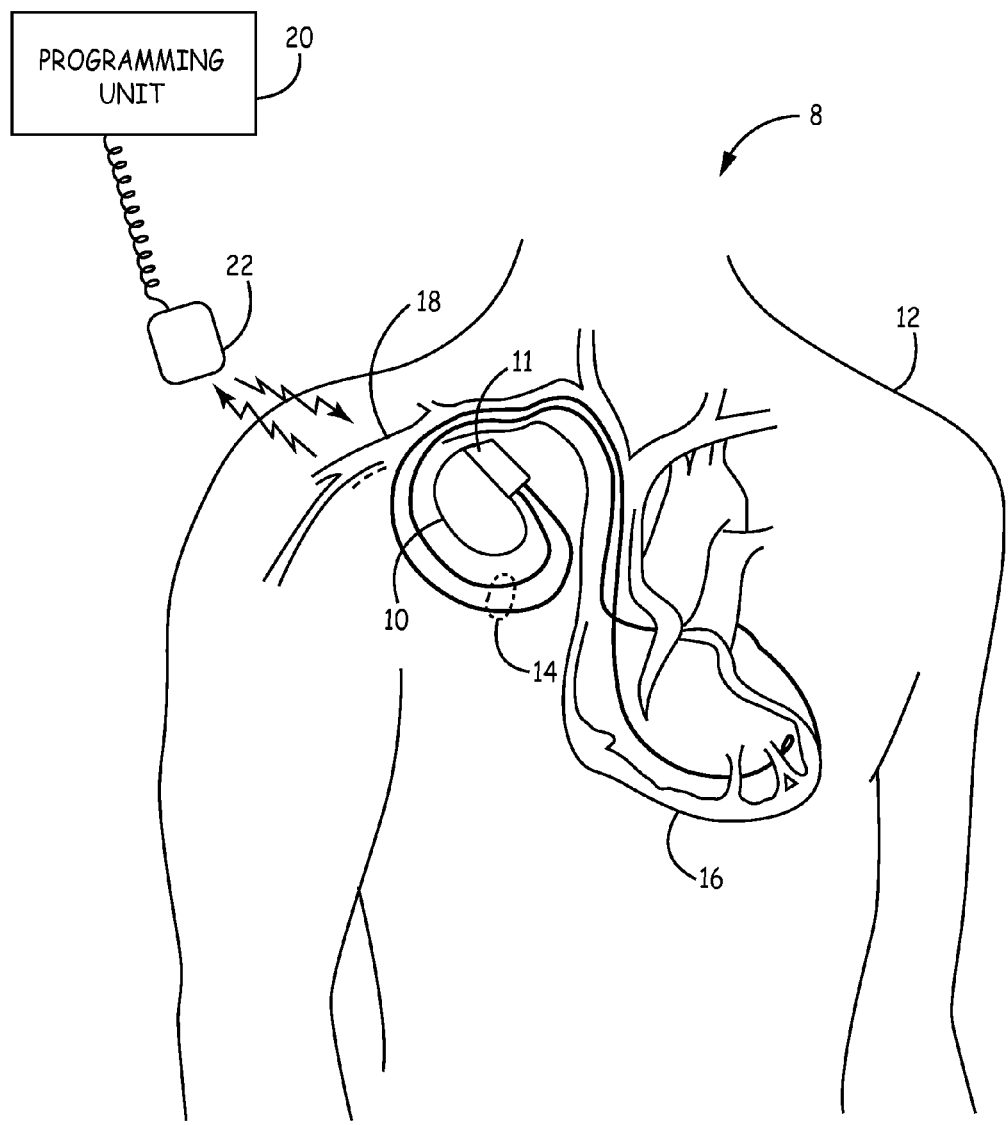
FIG. 1 illustrates an exemplary implantable medical system.

Within an implantable medical device (IMD), there are many discrete processes involving collecting, storing, and presenting physiologic trends of a patient, as well as in delivering therapies (e.g., a cardiac therapy). The battery located within the IMD provides the power necessary for performing such operations. The components utilized for performing each of the various functions draws a threshold amount of power (power level) from the finite source battery to perform its intended operation. Therefore, conserving battery power can provide for longer, uninterrupted operation of the IMD.

The present disclosure provides diverse methods and apparatus for in vivo monitoring, detecting and/or predicting potential device conditions or deleterious trends of a chronically implanted IMD. As used herein, a device condition generally refers to any fault or condition prohibiting or frustrating performance of the device in a predetermined manner during normal operation of the implantable medical system.

Exemplary implementations of the present disclosure facilitate monitoring of the device hardware to enable detection of leading indicators and system-critical indicators of potential issues including faults, anomalies, and degradation of performance. Such leading indicators and system-critical indicators may relate to such issues as the power source depletion, current drain by individual components or circuit blocks, storage capacity and integrity of the memory bits, etc. Other examples include, but are not limited to, parameters associated with physical conditions of the device such as sensed noise, lead impedance outside a predetermined range, capture failure, capture amplitude voltage outside a pre-determined range, intrinsic amplitude outside a predetermined range, failure to detect an expected event, and an electrical hardware failure.

Some faults that could potentially occur may be in ranges outside the normal sensing capability of many commercial sensors. In many IMDs, the leakage current is kept to a minimum and restricts the designs of discrete components and IC technologies that can be utilized—many of which exhibit ultra-low leakage. The increasing leakage current can alter the remaining useful life of the product, or in extreme cases, degrade the functionality of the device. Conventionally, monitoring the increase in the leakage currents has been difficult due to orders of magnitudes of the amount of leakage current relative to the baseline leakage. The ability to detect the leading indicators and system-critical indicators trending toward potential device degradation offers the opportunity to respond to potential faults even before the graduated degradation process occurs thereby minimizing the impact of a device condition to the patient.

To be effective, the prognostics are desired to provide appropriate sensitivity (ability of the prognostics to accurately identify true pre-emerging events) and specificity (ability of the prognostics to minimize false positive prognostic indications). In an implanted medical device application, any indication of a potential impending failure can be highly disruptive to the patient, and may lead to unnecessary intervention. As such, accurate prognostics that are actionable, in terms of identifying the root cause, rather than just indicating a potential fault are needed.

Another consideration is the prognostic time capability of the various sensors and algorithms. In particular, the prognostic time is desired to be at least on a timescale that is appropriate to permit early intervention based on the level of severity. In other words, the present disclosure facilitates identification of potential failures prior to adverse clinical outcomes.

FIG. 1 illustrates an implantable medical system 8, which includes, for example, an implantable medical device ("IMD") 10 that has been implanted in a patient 12. The IMD 10 is housed within a hermetically sealed, biologically inert outer canister or housing, which may itself be conductive so as to serve as an electrode in the pacing/sensing circuit. One or more leads, collectively identified with reference numeral 14 are electrically coupled to the IMD 10 in a conventional manner and extend into the patient's heart 16 via a vein 18. Disposed generally near a distal end of the leads 14 are one or more conductive electrodes for receiving electrical cardiac signals or delivering electrical pacing stimuli to the heart 16. The leads 14 may be implanted with their distal end situated in either the atrium or ventricle of the heart 16.

Although the disclosure is described herein in an embodiment that includes a cardiac device, it may be advantageously embodied in numerous other types of implantable medical systems in which it is desirable to optimize the energy consumption of an implanted device with a finite energy source.

With continued reference to FIG. 1, an external programming unit 20 is depicted for non-invasive communication with the IMD 10 via conventional uplink and downlink communication channels, which are not described in greater detail herein so as to avoid unnecessarily obscuring the details of the present disclosure. In an embodiment, the programming unit 20 may be associated with a programming head 22, in accordance with conventional medical device programming systems, for facilitating two-way communication between the IMD 10 and the programmer 20. In many known implantable systems, the programming head 22, such as that depicted in FIG. 1, is positioned on the patient's body over the implant site of the device 10 (usually within about 2 to about 3 inches, or equivalently, about 5 to about 8 cm, of skin contact), such that one or more antennas within the head 22 can send radio frequency (RF) signals to, and receive radio frequency (RF) signals from, an antenna (not shown) disposed within the hermetic enclosure of the implanted device 110 or disposed within a connector block 11 of the device 10, in accordance with common practice in the art.

Figure 2:
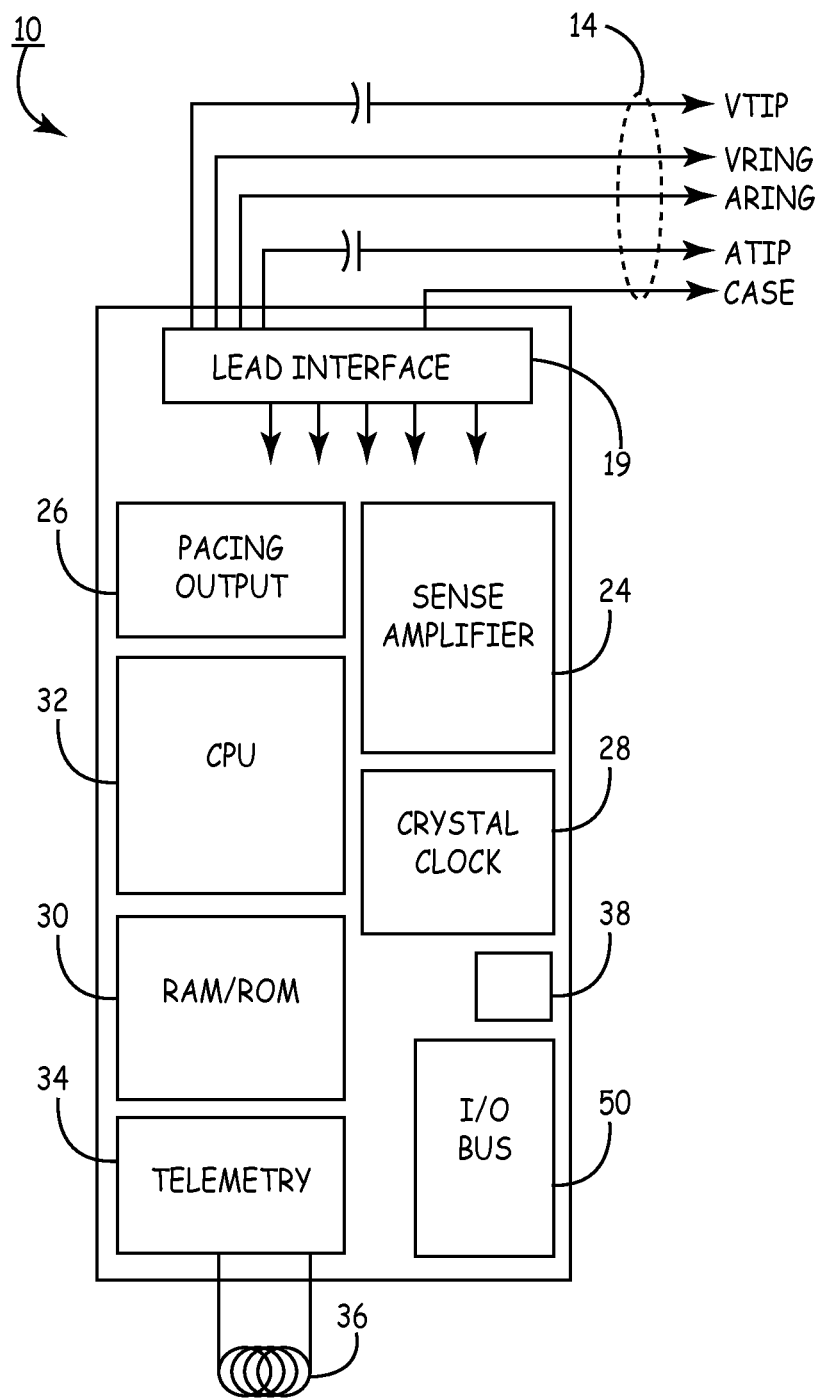
FIG. 2 depicts a block diagram of one exemplary embodiment of electronic circuitry for an implantable medical device (IMD)

FIG. 2 provides a general block diagram of electronic circuitry that makes up the IMD 10. The IMD 10 is a device capable of performing a variety of functions, such as delivering electrical stimulation therapy to the patient 12 in accordance with the presently disclosed embodiment of the disclosure. FIG. 2 shows that IMD 10 comprises circuitry for controlling the device's pacing and sensing functions. Aspects of the IMD circuitry may be of conventional design, in accordance for example, with what is disclosed in U.S. Pat. No. 5,052,388 issued to Sivula et al. and entitled "Method and Apparatus for Implementing Activity Sensing in a Pulse Generator." The '388 patent is hereby incorporated by reference herein in its entirety.

To the extent that certain components of the circuitry of the IMD 10 are conventional in their design and operation, such components will not be described herein in detail because it is believed that design and implementation of such components would be a matter of routine practice to those of ordinary skill in the art. For example, the circuitry of the IMD 10 shown in FIG. 2 includes sense amplifier circuitry 24, stimulating pulse output circuitry 26, a crystal clock 28, a random-access memory and read-only memory (RAM/ROM) unit 30, and a pacing timing and control circuit in the form of a programmed control unit 32. The control unit 32 may be a digital signal processing component such as a microprocessor or a microcontroller. While the embodiment of FIG. 2 refers to a digital signal processor-based architecture, it should be noted that other architectures, such as the logic or state machine architectures or other components or circuitry for performing a processing function, are contemplated in the present disclosure. Such architectures are not discussed in detail herein merely for the sake of brevity.

The control unit 32 may take the form one or more microprocessors, DSPs, ASICs, FPGAs, programmable logic circuitry, or the like, and the functions attributed to control unit 32 herein may be embodied as hardware, firmware, software or any combination thereof. Memory unit 30 may store instructions that cause control unit 32 to provide the functionality ascribed to IMD 10.

The functionality includes various techniques for detecting device conditions that may compromise the operation of a medical device, e.g., IMD 10. In the disclosed examples, an event-triggered prognostic indicator, e.g., implemented as a hardware module, software module, firmware module, or any combination thereof may be provided to identify device conditions by performing a diagnostic evaluation of a component associated with performing a function in response to leading indicators and system-critical indicators that may be indicative of a potential failure of one or more components of the IMD 10. In particular, the electrical characteristics of the component(s) may be obtained by the event-triggered prognostic indicator for the evaluation as will be discussed in more detail below. Briefly, the device conditions may be identified during the diagnostic evaluation by comparing one or more electrical characteristics/properties of the component(s) to one or more predetermined criteria such as a threshold or a range, or by evaluating trends, or through detection of morphological and timing deviations, or by monitoring a response to application of a test signal that is delivered to the component(s). If a leading indicator or system-critical indicator is obtained based on the monitored electrical properties, a device condition is identified.

In one example, the event-triggered prognostic indicator is capable of monitoring, collecting, measuring, and/or calculating various signals associated with the performance of the device components or physiological signals. The event-triggered prognostic indicator derives various parameters associated with the signals and these parameters may be stored in memory unit 30 for evaluation.

The IMD 10 also includes an internal telemetry communications circuit 34 coupled to an antenna 36 so that it is capable of communicating with the external programmer/control unit 20. Various telemetry systems for providing the uplink and downlink communication channels between the external programming unit 20 and the IMD 10 have been shown in the art and may be employed herein without departing from the spirit and scope of the disclosure.

With continued reference to FIG. 2, the IMD 10 is coupled to one or more leads 14 which, when implanted, extend transvenously between the implant site of the IMD 10 and the patient's heart 16, as previously noted with reference to FIG. 1. Physically, the connections between the leads 14 and the various internal components of the IMD 10 are facilitated by a conventional connector block assembly 11, shown in FIG. 1. Electrically, the coupling of the leads 14 and the internal electrical components of the IMD 10 may be facilitated by a lead interface circuit 19, which functions, in a multiplexer-like manner, to selectively and dynamically establish necessary connections between various conductors in the leads 14, including, for example, atrial tip and ring electrode conductors ATIP and ARING and ventricular tip and ring electrode conductors VTIP and VRING, and individual electrical components of the IMD 10, as would be familiar to those of ordinary skill in the art. For the sake of clarity, the specific connections between the leads 14 and the various components of the IMD 10 are not shown in FIG. 2, although it will be clear to those of ordinary skill in the art that, for example, the leads 14 will necessarily be coupled, either directly or indirectly, to sense amplifier circuitry 24 and stimulating pulse output circuitry 26, in accordance with common practice, such that cardiac electrical signals may be conveyed to the sense amplifier circuitry 24, and such that stimulating pulses may be delivered to cardiac tissue, via the leads 14.

It will be appreciated that the signals received over the leads 14 by the sense amplifier circuitry 24 may be collected and stored in the RAM/ROM unit 30 by the control unit 32 acting under control of software also stored in the RAM/ROM unit 30. Additional data, such as the timing of signals delivered by the stimulating pulse output circuitry 26 may also be stored in the RAM/ROM unit 30. This stored data may be later retrieved and delivered to the programming unit 20 via the telemetry communications circuit 34.

IMD 10 may transmit information regarding device conditions to programmer 20 via telemetry communications circuit 34. For example, IMD 10 may provide processing results or other sensed signal to an external device, such as the programmer 20, for additional processing and/or confirmation of identification of device conditions. In some examples, the processing results from numerous evaluation phases may be transmitted to the programmer 20 for identification of possible trends illustrating the performance of the IMD 10 over time. IMD 10 may also receive information regarding device conditions or responses to such conditions from programmer 20 via telemetry communications circuit 34 and/or receive user approval of a response.

As previously noted, the circuitry of the IMD 10 includes the control unit 32 which may be an off-the-shelf programmable microprocessor or microcontroller, but in the presently illustrated embodiment of the disclosure is a custom integrated circuit. Although specific connections between the control unit 32 and other components of the IMD circuitry are not shown in FIG. 2, it will be apparent to those of ordinary skill in the art that the control unit 32 functions to control the timed operation of the stimulating pulse output circuit 26 and the sense amplifier circuit 24 under control of a program of instructions stored in the RAM/ROM unit 30.

In one embodiment, clock 28 in the presently illustrated embodiment is a crystal controlled oscillator that provides a main timing clock signal to other components of IMD 10. In another embodiment, the clock 28 may include a clock generator such as a crystal oscillator for providing a clock signal of a given frequency and a programmable frequency divider for generating multiple clock signals of different frequencies based on the first clock signal and for outputting one of the multiple clock signals. The lines over which the aforementioned clock signals are provided to the various components of the IMD 10 (e.g., the control unit 32) are omitted from FIG. 2 for the sake of clarity. It is believed that those of ordinary skill in the art will be familiar with such an operative arrangement.

It is to be understood that the various components of the IMD 10 depicted in FIG. 2 are powered by means of a battery 38, which is contained within the hermetic enclosure of the IMD 10, in accordance with common practice in the art. For the sake of clarity in the drawings, the connections between the battery and the other components of the IMD 10 are not shown.

In accordance with various aspects, the event-triggered prognostic indicator will consume less power to derive the various parameters from the sensor data in comparison to the power consumption required to perform the diagnostic evaluations. As such, long term continuous and/or real-time monitoring of the leading indicators and/or system-critical indicators may be performed without impacting performance and longevity of the IMD 10.

Those of ordinary skill in the art will appreciate that the IMD 10 may include numerous other components and subsystems, for example, activity sensors and associated circuitry. The presence or absence of such additional components in the IMD 10, however, is not believed to be directly pertinent to the disclosure, which relates generally to optimizing operation of the microcontroller to minimize power consumption and promote an extension of the life of the energy source.

Stimulating pulse output circuitry 26, which functions to generate cardiac stimuli under control of signals issued by the control unit 32, may be, for example, of the type disclosed in U.S. Pat. No. 4,476,868 to Thompson, entitled "Body Stimulator Output Circuit," which patent is hereby incorporated by reference herein in its entirety. Again, however, it is believed that those of ordinary skill in the art could select from among many various types of prior art pacing output circuits, which would be suitable for the purposes of practicing the disclosure. The sense amplifier circuitry 24, may be, for example, of the type disclosed in U.S. Pat. No. 4,357,943 to Thompson, entitled "Demand Cardiac Pacemaker Having Reduced Polarity Disparity," which patent is hereby incorporated by reference herein in its entirety.

Generally, the sense amplifier circuitry 24 functions to receive electrical cardiac signals from the leads 14 and to process such signals to derive intrinsic event signals reflecting the occurrence of specific cardiac electrical events, including atrial contractions (P-waves) and ventricular contractions (R-waves). These event-indicating signals are provided to the control unit 32 for use by the control unit 32 in controlling the synchronous stimulating operations of the IMD 10 in accordance with common practice in the art. In addition, these event-indicating signals, as discussed above, may be communicated, via the uplink communication channel, to the external programming unit 20 for storage and visual display to a physician or clinician.

It is important to note that leadless embodiments of the present disclosure are also contemplated, where one or more stimulation and/or sensing electrode capsules or modules are implanted at or near a desired target tissue site, and the capsules or modules deliver electrical stimuli directly to the site using a preprogrammed stimulation regime, and/or the capsules or modules sense electrical or other pertinent signals.

In addition to the sensed physiologic events, it is contemplated that additional activities will give rise to a need for signal processing. As such, "events" as used in the present disclosure refer to physiological activities, data handling requests, or functions performed by the device that may necessitate a processing function being performed by the control unit 32. Examples of such events include an intrinsic cardiac condition, a stimulation therapy signal, noise interference, and numerous other activities, any of which result in a processing action to be performed by the control unit 32.

Figure 3:
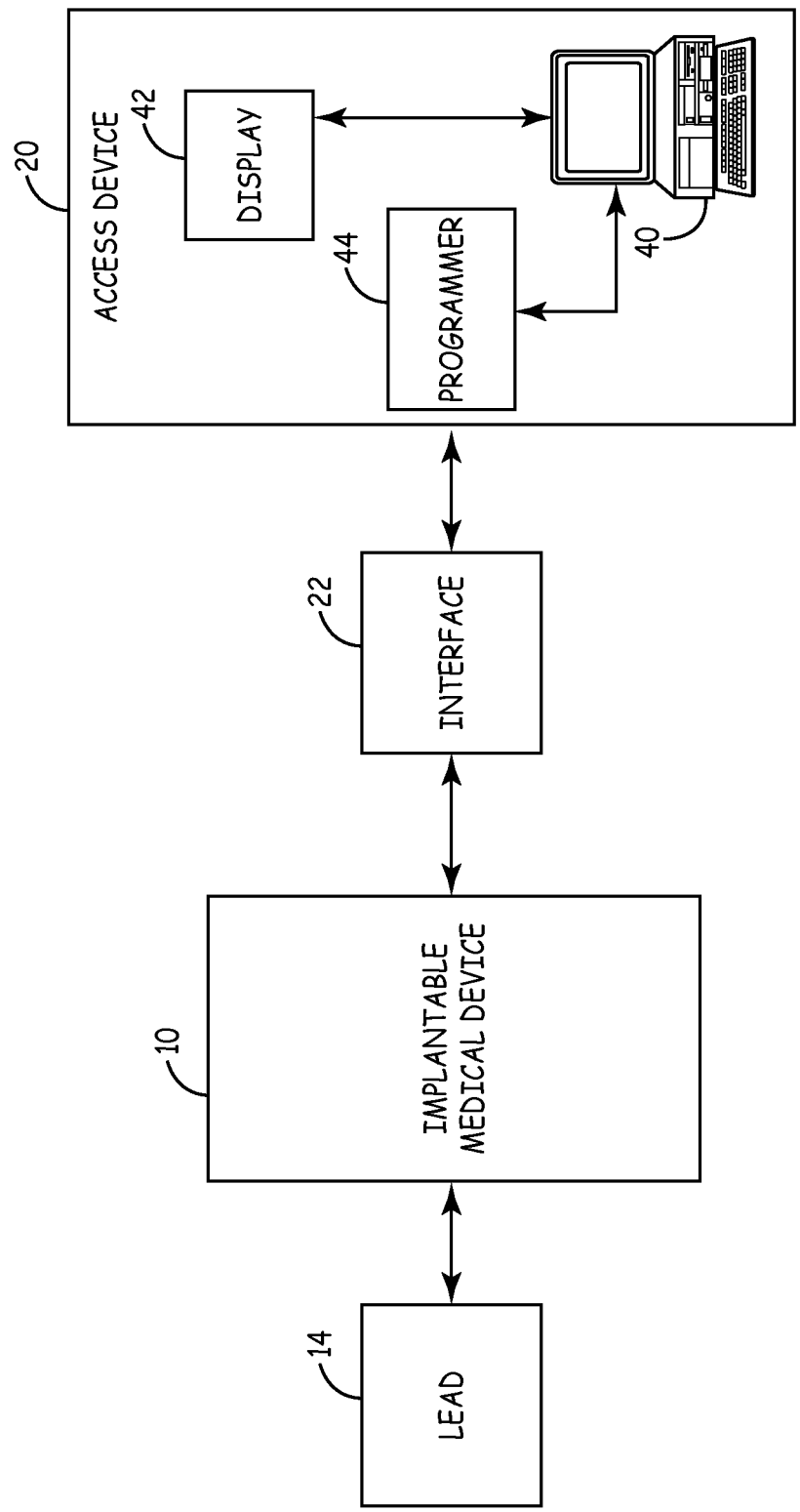
FIG. 3 illustrates an external programmer associated with the IMD.

FIG. 3 illustrates a more detailed illustration of the external programmer/control unit 20. In one embodiment, the programmer/control unit 20 comprises a computer system 40, a display device 42, and a processing unit 44. In one embodiment, the processing unit 44 can be integrated into the computer system 40. The computer system 40 can prompt the acquisition of physiologic data from the cardiac IMD 10 via the programming head 22. The computer system 40 can then display the physiologic data on the display device 44. The display device 44 can display physiologic data from the reference point of different time periods, different activity results, and the like.

A user may use programmer 20 to select therapy programs (e.g., sets of stimulation parameters), generate new therapy programs, modify therapy programs through individual or global adjustments or transmit the new programs to IMD 10 in response to detection of a fault.

The user may also use programmer 20 to adjust or control the detection of device conditions performed by IMD 10. For example, the user may use programmer 20 to program the thresholds to which delivered energy and lead impedance are compared, or any other aspects of the fault detection. In this manner, the user may be able to fine tune the detection of specifically-targeted potential faults. In some examples, the user uses programmer 20 to control the performance of a fault detection for detecting device conditions, e.g., in a clinic, hospital, or operating room setting, at the time of implant or during a follow-up visit.

In addition, the user may receive an alert from IMD 10 indicating a potential device condition via programmer 20. The user may respond to IMD 10 by suggesting a response to a detected device condition. Alternatively, IMD 10 may automatically suggest a response to a lead-related condition. Programmer 20 may prompt the user to confirm the response.

In accordance with embodiments of this disclosure, a range of prognostic parameters that span from continuous to periodic measurements of device and component behaviors are monitored to identify the presence of potential faults. The prognostic parameters may be derived from a range of sources that provide signals pertaining to device performance and sensed physiological signals. For example, the prognostic parameters may be derived from the physiological signals sensed by leads 14 from the heart 16. Different potential faults can be identified in the transmission pathway of the lead 14 including micro-dislodgement at the lead to cardiac tissue interface, fractures, insulation breaches, or intermittencies at the connection interface of the proximal end of lead 14 to the connector at block 11. In addition, because the human body is only physically capable of physiological heart rates within certain ranges, signals of short, non-physiological intervals between sensing operations of cardiac events may be monitored to help detect intermittencies and potential system noise in the sensed signal or the connection interface.

Other examples of the sources from which the prognostic parameters are derived include the mechanical and electrical signals associated with the operation of the device. Such mechanical and electrical signals may include device functions pertaining to therapy delivery and sensing. The signals may be derived from measurements of lead 14 and the tissue-to-lead interface such as impedance and amplitude stability of the sensed cardiac events (e.g. cardiac P and R wave amplitudes).

Figure 4:
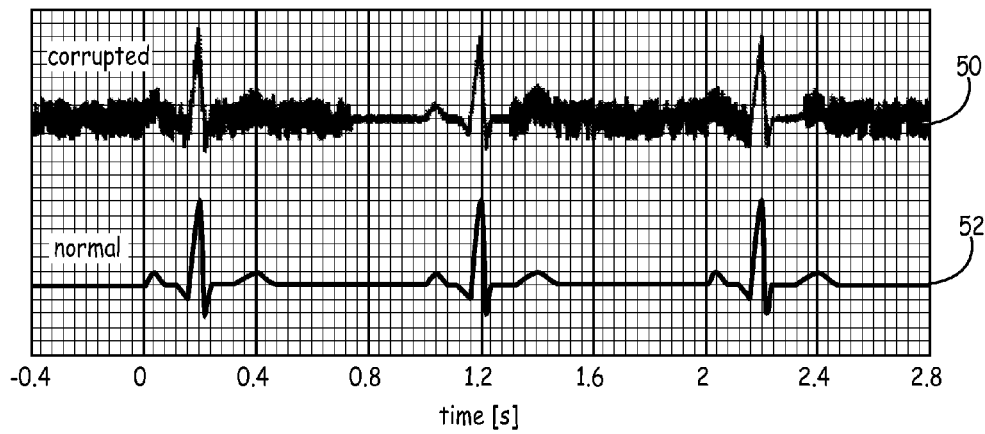
FIG. 4 depicts comparative views of cardiac waveforms.

FIG. 4 depicts comparative views of cardiac waveforms. Signal 50 illustrates a noisy cardiac signal whereas signal 52 illustrates an uncorrupted cardiac signal. In signal 50, the cardiac signal is shown including noise that may be associated with a lead fracture or a poor lead connection. This type of noise can result in saturation of the sense amplifiers and intermittent bursts of noise. Oversensing due to a lead fracture or poor lead connection, therefore, produces intermittent clusters of sensed events, as shown in the signal 50.

As seen in the noisy signal 50, non-cardiac oversensing is generally associated with multiple oversensed events per cardiac cycle that may be intermittent or continuous, of high or low amplitude, and of relatively low or high frequency. The repeated detection of non-sustained cardiac episodes, such as short bursts of ventricular fibrillation, which self-terminate may be indicative of improper sensing due to issues such as lead malfunction, high levels of external electromagnetic interference, or lead placement/stability issues, and are not likely to have a true physiological origin. Individually, lead pathway impedance trends and short interval counts may not identify such abnormalities especially during the early stages of emergence of the fault condition.

Conventional techniques have utilized such trends and counts as measures of lead pathway and sensing integrity to detect abrupt changes, such as a sudden impedance change from 500 Ohms to impedances greater than 8000 Ohms on a sensing pathway. However, detection of an abrupt change that has a clinical impact (e.g. loss of pacing due to lead fracture) may not provide an adequate response time for intervention and may not provide early detection of emerging issues.

In contrast to signal 50, the signal 52 depicts sensed events that are typical of the cyclical nature of a cardiac cycle. The presence of non-physiological noise on the signal 50 may be detected by filtering the signal and comparing it to the raw unfiltered sensed signal to obtain a measure of lead integrity or possible exposure to environmental electromagnetically introduced noise sources.

Figure 5:
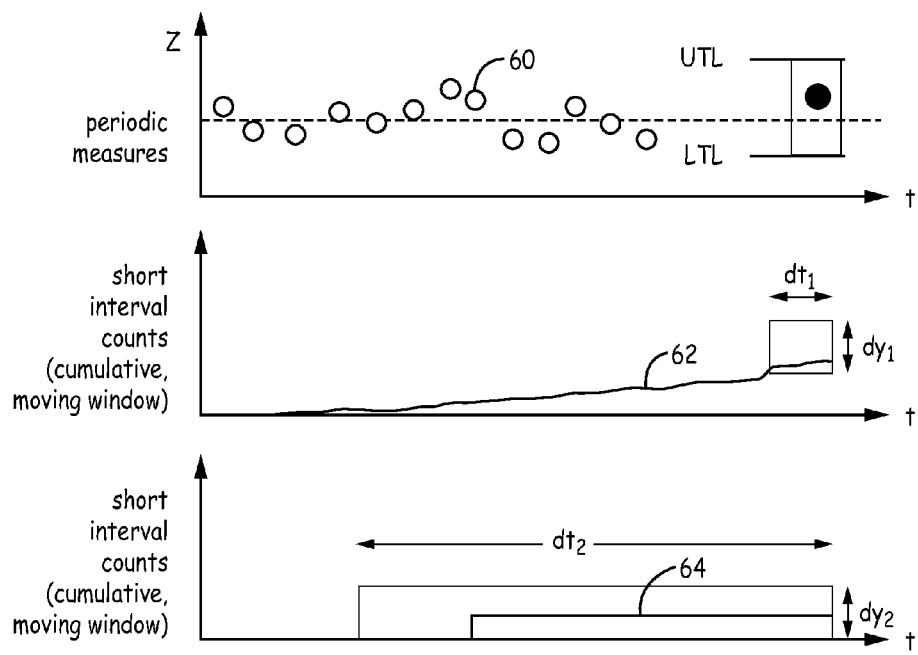
FIG. 5 illustrates multiple signals that are utilized in accordance with one embodiment to identify a potential fault of a component.

FIG. 5 illustrates multiple signals 60, 62, 64 that are utilized in accordance with one embodiment to identify a potential fault of a component. The signals may be viewed as containing data subsets of a larger data set or separate sets of data. Two or more of the signals 60, 62, 64 may be combined to facilitate the earlier detection of emerging faults with greater sensitivity and specificity to a given fault by obtaining one or more leading indicators or system-critical indicators. For example, signals 100, 102, and 104 may be utilized together, or in any combination of two, to detect statistical differences in lead impedance measurements compared to a recent baseline of measurements (similar to statistical process control triggers), counts of non-physiological short sensed event intervals, and/or the observation of non-sustained cardiac episodes that suddenly appear and then self-terminate. Individually, any of the signals 100, 102, or 104 may not provide sufficient sensitivity and specificity to detect a large enough percentage of real, potential sensing issues due to lead integrity, but in combination, the overall efficiency is increased to enable detection of emerging faults.

A prognostic threshold may be predefined to indicate criteria that will trigger a diagnostic evaluation of the component that is associated with the evaluated signal(s) for detection of the potential fault. In an implementation, the criteria may be defined by a prognostic threshold that is comprised of multiple values, with a single one of the values being applicable for a given one of the individual signals. Continuing with the implementation, the triggering of the diagnostic evaluation occurs responsive to a result of the collective evaluation of the signals. In other words, in response to the result of the evaluation of one or more of the individual signals exceeding the respective prognostic threshold value, the diagnostic evaluation is triggered. In accordance with the implementation, the relative inaccuracies related to the evaluation of each individual signal are balanced out by the results of the collective evaluation and any weighted averages that may be assigned to each, thereby providing consistency and increased accuracy in the prediction of potential faults—relative to an evaluation of any given signal individually. This greater accuracy ensures better prognostic information for detection of potential faults for advance intervention.

Further, additional actions may be performed in response to the criteria being met. For example, the values defining the criteria for triggering the diagnostic evaluation may be modified and/or a notification may be generated. The notification may include one or both of an IMD generated alarm (auditory and/or sensory) or an alert generated by an external device.

Table 1, below, provides additional examples of signals that may be sensed and/or monitored under the normal operation mode for derivation of prognostic parameters and determination of instances resulting in diagnostic evaluation. It should be noted that the list is not intended to be limiting, but rather that other signals and sources of those signals within the spirit and scope of those discussed herein are contemplated. The items in each row correspond to the signals from which plurality of parameters associated with a function of the IMD (left-hand column) and the corresponding operations (right-hand column) that may be performed during a diagnostic evaluation that is activated based on the results of an evaluation of the plurality of parameters.

TABLE I examples of event triggered system prognostics

| Normal Operation Mode | Diagnostic Evaluation |
|---|---|
| Short-interval count(s) detected | Perform lead impedance measurement (continuous and/or real-time snapshot in time measurement) Perform sensing circuit fault detection check (e.g. change frequency of the protection circuitry for the charge pump to determine if noise is potentially corrupting a signal) |
| Non-sustained VT episode detected | Perform lead impedance measurement (continuous and/or snapshot in time measurement) Perform sensing circuit fault detection check (e.g. change frequency of the protection circuitry for the charge pump to determine if noise is potentially corrupting a signal) |
| Short-interval count on pathway containing HV elements (e.g. RV Coil) | Perform HV lead impedance measurement (e.g. real-time, continuous measurement for x seconds) |
| Non-sustained VT detected on pathway containing HV elements (e.g. RV Coil) | Perform HV lead impedance measurement (e.g. real-time, continuous measurement for x seconds) |
| Lower than expected battery voltage | Perform real-time current drain measurement Perform real-time battery impedance |

TABLE I-continued examples of event triggered system prognostics

| Normal Operation Mode | Diagnostic Evaluation |
|---|---|
| Pacing hold cap amplitude monitor (e.g. delta-V) out of range (this is a paced beat-to-beat measurement in real-time) | measurement<br>Measure individual supply voltage levels<br>Perform lead impedance measurement<br>Perform capture management (option: if more than n of m delta-V violations)<br>Perform P/R wave amplitude check |
| High rate sensing (potential VT/VF episode) | Perform sensing on a disconnected channel for signs of non-cardiac signals (e.g. circuit fault or EMI)<br>Perform sensing circuit fault detection check (e.g. change frequency of the protection circuitry for the charge pump to determine if noise is potentially corrupting a signal) |
| SRAM (non-flash) memory fault (e.g. bit flip) detected and corrected by error correction and detection (EDAC) | Perform memory scrubbing algorithm to check (and correct) memory space during next suitable interval. |
| Flash memory fault (e.g. previously unobserved corrupted bits) detected and corrected by EDAC | Perform a flash memory check to look for additional flash memory faults. |
| Pacing hold cap leakage | Perform lead impedance measurement<br>Perform capture management (option: if more than n of m delta-V violations)<br>Perform P/R wave amplitude check |
| HV delivery short (any pathway) | Perform HV lead impedance (after episode is dealt with) - all pathways |
| HV delivery open or out of range high resistance (any pathway) | Perform HV lead impedance (after episode) - all pathways |
| Device Power on Reset | Perform all normally scheduled daily checks (e.g. lead impedance, P/R waves, capture management, etc.) after POR is resolved and any episodes are handled |

In accordance with the scope of the present disclosure, the prognostics may apply to components or to functional circuit block(s). For example, the principles of this disclosure may be utilized to detect the emergence of potential faults occurring in a memory unit. In that example, the event-triggered prognostic indicator will utilize signals pertaining to the error detection and correction data that is typical of single event occurrences of memory fault for obtaining leading indicators or system-critical indicators. The data pertaining to the error detection and correction is subsequently analyzed to generate parameters indicating the utilization of error correction due to memory corruption. Those parameters are analyzed through a comparison to a threshold, for example, indicating the predetermined value that represents the desired level of memory integrity. For example, the values associated with the threshold levels may be linked to exposure to certain medical therapies (such as cancer radiotherapy equipment) or could indicate an underlying performance issue with the memory component. In other examples, a trend analysis may also be performed to determine whether a single memory bit is impacted or if a more ominous trend of increasing memory corruption is encountered. Based on a result indicating that the predetermined threshold has been exceeded, a comprehensive memory correction technique, e.g., memory scrubbing, may be performed.

In another example, the principles of this disclosure may be utilized to detect the emergence of potential faults occurring in a circuit block(s) associated with therapy delivery. In this example, the event-triggered prognostic indicator will utilize signals pertaining to the energy delivered to the heart as well as the performance of the charging system to obtain the leading indicators or system-critical indicators. The signals may include data on changes in charging performance that may trigger additional signals to be obtained such as the lead impedance and other lead integrity checks. Continuing with the example, the combined evaluation of the various signals to determine whether the respective thresholds have been met will trigger a diagnostic evaluation of the circuit block for a determination of a potentially faulty circuit component that is draining more power than expected, or whether the lead integrity has been compromised resulting in the increased energy demand.

In some examples, the signals utilized by the event-triggered prognostic indicator may be derived from measurements associated with device functionality. One such measurement may be a comparison of the actual energy discharged during therapy delivery through the conductors to a pre-determined percentage value stored in memory unit 30. When a fault is present, the therapy delivery circuitry will generate and deliver the programmed energy in the form of a voltage or current pulse to the electrical path defined by the lead, with the energy actually delivered being diminished due to the device condition. In order to identify the device condition, therefore, the event-triggered prognostic indicator may determine whether the energy delivered is less than a pre-determined percentage of the programmed energy of the delivered signal. In some examples, the threshold percentage of programmed energy is in a range from approximately 60% to approximately 80%. In one example, the threshold percentage of programmed energy is approximately equal to 75%.

As another example, the leading indicators and system-critical indicators may be obtained from signals associated with the feedback utilized in a given circuit block(s) to continuously adjust the operating conditions for normal operation under various use conditions. The signals may include the voltage at a specific node for identification of deviations in expected ranges as a function of the established threshold. Based on the deviation information, a diagnostic evaluation may be triggered to isolate or clearly identify a root cause of a potential fault.

Thus, the parameters generated from the sensed signal and that are available on a real-time basis can be evaluated to generate the leading indicators and system-critical indicators thereby triggering the diagnostic evaluation responsive to threshold limits being exceeded. Accordingly, a reduction in the prognostic time is achieved because the diagnostic evaluation of the component(s) is immediately triggered based on the real time sensed data.

Figure 6:
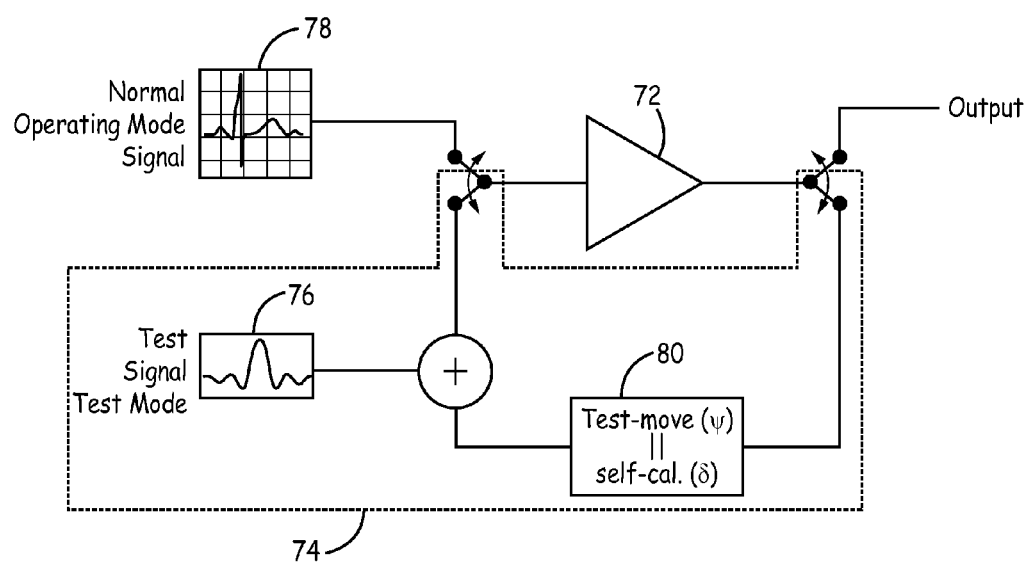
FIG. 6 illustrates an embodiment of a circuit for performing diagnostic evaluation of a circuit block.

FIG. 6 illustrates an embodiment of a circuit for performing diagnostic evaluation of a circuit block. The circuit 70 may be utilized to evaluate one or more component(s) deemed to have a potential fault based on the threshold evaluation of parameters derived from a sensed signal. In the circuit 70, a circuit block 72 having the one or more components to be evaluated is coupled to a test block 74. The test block 74 includes a signal generator 76 that generates a test signal for the evaluation of the circuit block 72. The test signal may be similar to a manufacturing test signal that is utilized to trim the circuit block 72. The component(s) in the circuit block 72 to be evaluated may be taken off-line temporarily and connected from the rest of the IMD 10 circuits that provide actual-use signals 78 to the circuit block 72. The test block 74 also includes event-triggered prognostic indicator module 80 that in this implementation performs various evaluations of the functionality of circuit block 72.

For example, various adjustable parameters may be utilized to assess the trimming of the circuit block 72. Over time, drifts or sudden changes in the trim values may be an indicator of an emerging issue. The trim values may be linked to previously characterized failure modes in a particular implementation, with additional considerations for potential fault-tolerance in the design. Depending on the scope of detail that is appropriate to isolate or correct the potential fault, the diagnostic evaluation can be applied to blocks of circuitry or to more discrete component(s) to identify the root cause of the potential failure.

Figure 7:
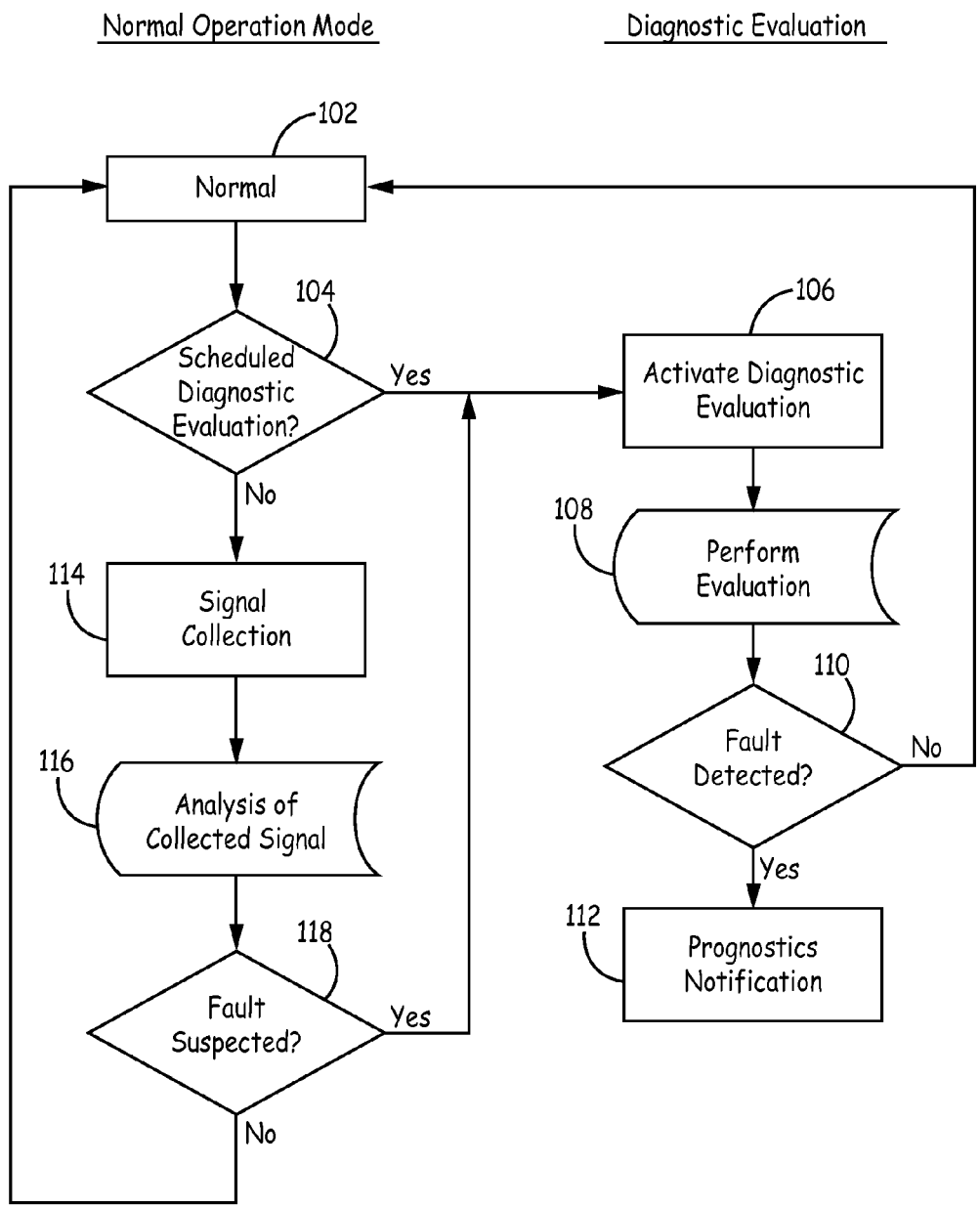
FIG. 7 is a flowchart illustrating a method performed by an event-triggered prognostic indicator for identification of a potential failure with an IMD.

FIG. 7 is a flowchart illustrating a method performed by an event-triggered prognostic indicator for identification of a potential failure with an IMD. The functions of the event-triggered prognostic indicator may be implemented logically and/or physically as a separate module within IMD 10 or within control unit 32. For example, IMD 16 may include an event-triggered prognostic indicator having various modules for performing functions related to identifying faults within various circuit blocks. One or more modules of the event-triggered prognostic indicator may additionally or alternatively be embodied in other digital or analog circuitry. The modules of the event-triggered prognostic indicator may be embodied as one or more hardware modules, software modules, firmware modules, or any combination thereof.

In the method 100 of FIG. 7, a plurality of parameters associated with a function of the IMD are derived from a sensed signal and evaluated to generate leading indicators and/or system-critical indicators based on comparisons to preset criteria. The comparisons may involve, for example, threshold crossing determinations and out-of-range determinations or template comparisons. In response to the results of the comparison, a diagnostic evaluation of a component associated with the function is activated. In an embodiment, an evaluation based on two or more signals may be used to trigger the diagnostic evaluation. In yet other embodiments, a combination of the derived signals and the result of the diagnostic evaluation may be utilized to identify a potential fault. While the embodiment is illustrated in conjunction with the IMD, alternative embodiments may be implemented having one or more of the tasks being performed by the external monitors, programmers, or other external instruments. This may reduce some power and analysis complexity burdens in implementing the event-triggered prognostics.

At task 102, an implantable medical device (IMD) is initialized in a normal operation mode. In the normal operation mode, the IMD receives real-time signals that are either sensed or generated during operation of the device. A determination is made as to whether a comprehensive diagnostic evaluation has been scheduled (104) for the components or circuit block associated with the sensing or generation of the signals. If scheduled, the diagnostic evaluation is activated (106).

Otherwise, if a diagnostic evaluation is not scheduled, the received real-time sensed signals or generated signal data are monitored and collected for a determination of a potential fault (114). In particular, a first plurality of parameters may be derived from the sensed signal. The parameters are subsequently evaluated to determine whether the signal provides an indication of a suspected fault (116). This determination may involve threshold comparisons, or trending analysis, or range classifications, or any other analysis technique that may provide an indication of a fault. The results of the analysis are evaluated to determine whether there is a likelihood of an unconfirmed potential fault (118). If so, the diagnostic evaluation may be activated (106). Otherwise, the normal operating mode continues.

Continuing with task 106, the diagnostic evaluation is performed on one or more component(s) associated with the sensing or generation of the real-time signals. In the diagnostic evaluation, additional parameters pertaining to the component(s) is obtained, monitored, and/or measured pertaining to operation of the device. The parameters may include input information (such as current and voltage levels, or signals from other components) or usage information (such as power drain or computation aspects) or output information (such as computation results or sensed parameters), etc.

Under control of the event-triggered prognostic indicator, the diagnostic evaluation may include a trending analysis that is performed to identify trends in the additional parameters (108). Further, additional data associated with the device function or sensing function performed by the component(s) may be obtained for a comprehensive analysis of the component(s). The additional data may be collected from the same source (e.g., historical data for a more in-depth analysis) or may be obtained from separate sources to confirm or supplement the analysis. Within each of these data types, there may be multiple sets of data such that a first subset is utilized during the normal operation mode and a second subset is combined with the first subset during the diagnostic evaluation for a more comprehensive assessment. As such, the trend identification may include generation of statistical distributions of any one or all the sets of data that is analyzed during the diagnostic evaluation.

The parameters generated from the diagnostic evaluation are compared to a threshold or a template or a range to pre-determined values (110). In alternative embodiments, the trend information is analyzed relative to predefined values to identify divergence of the parameters.

The results of the diagnostic evaluation will yield a determination as to whether a potential failure of the component(s) associated with the function is present. In response to the results indicating the presence of a potential fault, the patient and/or other users interacting with the IMD system may be notified (112). The type of notification is based on the potential severity of the fault, with a real-time notification being provided for significant faults as may be pre-determined by a user while a notification of other faults is provided during routine follow-up checks of the IMD. Real-time alerts may be communicated to the patient via an alert such as an audible tone or a vibratory mechanism. Otherwise, if the results indicate that a potential fault is not present, then the IMD resumes the normal operating mode.

In accordance with aspects of this disclosure, the inventors have observed that the results of the diagnostic evaluation will provide a degree of accuracy of the potential failure of the component that is greater than the degree of accuracy associated with the information that is provided during the normal mode of operation pertaining to the potential failure.

As previously stated, the event-triggered prognostic indicator will consume less power when operating in the normal operation mode as compared to the power consumed while operating in the diagnostic evaluation mode. As such, long term continuous and/or real-time monitoring of the leading indicators and/or system-critical indicators may be performed without impacting performance and longevity of the IMD.

While the disclosure is susceptible to various modifications and alternative forms, specific embodiments thereof have been shown by way of example in the drawings and are herein described in detail. It should be understood, however, that the description herein of specific embodiments is not intended to limit the disclosure to the particular forms disclosed, but on the contrary, the intention is to cover all modifications, equivalents, and alternatives falling within the spirit and scope of the disclosure as defined by the appended claims.

What is claimed is:

1. An implantable medical device having an event-triggered prognostic indicator, comprising:
   a sensor operatively configured to derive a first plurality of parameters associated with a function of the implantable medical device;
   memory configured to store information corresponding to the first plurality of parameters;
   a control module configured to:
      evaluate the first plurality of parameters to determine whether a first threshold has been exceeded, and
      activate a diagnostic evaluation of a component associated with performing the function in response to the first threshold being exceeded,
      wherein the first threshold corresponds to a potential failure of the component;
   a power source, wherein a first amount of power is drawn from the power source to derive the first plurality of parameters and a second amount of power, that is greater than the first amount, is drawn from the power source to activate the diagnostic evaluation.

2. The implantable medical device of claim 1, wherein the diagnostic evaluation comprises:
   measuring a second plurality of parameters that is associated with the first plurality of parameters; and
   analyzing the second plurality of parameters to detect a deviation of an operation of the sensor from a predetermined threshold.

3. The implantable medical device of claim 2, wherein the second plurality of parameters are measured from one or more sources that are different than the sources of the first plurality of parameters.

4. The implantable medical device of claim 1,
   wherein the first plurality of parameters provides a first degree of accuracy of the potential failure of the component and a result of the diagnostic evaluation provides a second degree of accuracy, that is greater than the first degree of accuracy, of the potential failure.

5. An implantable medical device having an event-triggered prognostic indicator, comprising:
   a sensor operatively configured to derive a first plurality of parameters associated with a function of the implantable medical device;
   memory configured to store information corresponding to the first plurality of parameters; and
   a control module configured to:
      evaluate the first plurality of parameters to determine whether a first threshold has been exceeded, and
      activate a diagnostic evaluation of a component associated with performing the function in response to the first threshold being exceeded,
      wherein the first threshold corresponds to a potential failure of the component;
      wherein the first plurality of parameters provides a first degree of accuracy of the potential failure of the component and a result of the diagnostic evaluation provides a second degree of accuracy, that is greater than the first degree of accuracy, of the potential failure; and
   wherein the result of the diagnostic evaluation provides a prediction of the potential failure of the component.

6. An implantable medical device having an event-triggered prognostic indicator, comprising:
   a sensor operatively configured to derive a first plurality of parameters associated with a function of the implantable medical device;
   memory configured to store information corresponding to the first plurality of parameters;
   a control module configured to:
      evaluate the first plurality of parameters to determine whether a first threshold has been exceeded, and
      activate a diagnostic evaluation of a component associated with performing the function in response to the first threshold being exceeded,
      wherein the first threshold corresponds to a potential failure of the component;
      wherein a notification is generated in response to a prediction of the presence of the potential failure of the component; and
      wherein the result of the diagnostic evaluation provides a prediction of the potential failure of the component; and
   a power source, wherein a first amount of power is drawn from the power source to derive the first plurality of parameters and a second amount of power, that is greater than the first amount, is drawn from the power source to activate the diagnostic evaluation.

7. The implantable medical device of claim 6, wherein the notification is selected from one of a patient alarm and an externally-generated alert.

8. The implantable medical device of claim 1, wherein the first plurality of parameters is associated with a physiological sensed event.

9. The implantable medical device of claim 1, wherein the first plurality of parameters is associated with an operative event of the implantable medical device.

10. The implantable medical device of claim 1, wherein the first plurality of parameters are derived in real time relative to the performance of the function.

11. The implantable medical device of claim 1, wherein the first threshold includes a predetermined range of values for the implantable medical device.

12. The implantable medical device of claim 1, further comprising determining a set of parameters associated with the component, wherein the first plurality of parameters corresponds to a first subset of the set of parameters and the second plurality of parameters corresponds to a second subset of the set of parameters.

* * * * *